United States Patent
Majeed et al.

(10) Patent No.: US 12,233,032 B2
(45) Date of Patent: Feb. 25, 2025

(54) COMPOSITIONS FOR MANAGEMENT OF POLYCYSTIC OVARY SYNDROME

(71) Applicants: Muhammed Majeed, Bangalore (IN); Kalyanam Nagabhushanam, East Windsor, NJ (US); Sarang Bani, Bangalore (IN); Anjali Pandey, Bangalore (IN)

(72) Inventors: Muhammed Majeed, Bangalore (IN); Kalyanam Nagabhushanam, East Windsor, NJ (US); Sarang Bani, Bangalore (IN); Anjali Pandey, Bangalore (IN)

(73) Assignee: Sami-Sabinsa Group Limited, Bangalore (IN)

( * ) Notice: Subject to any disclaimer, the term of this patent is extended or adjusted under 35 U.S.C. 154(b) by 368 days.

(21) Appl. No.: 17/732,655

(22) Filed: Apr. 29, 2022

(65) Prior Publication Data
US 2022/0347120 A1  Nov. 3, 2022

Related U.S. Application Data

(60) Provisional application No. 63/182,166, filed on Apr. 30, 2021.

(51) Int. Cl.
| | |
|---|---|
| *A61K 31/12* | (2006.01) |
| *A61K 9/00* | (2006.01) |
| *A61K 9/16* | (2006.01) |
| *A61K 9/20* | (2006.01) |
| *A61K 9/48* | (2006.01) |

(Continued)

(52) U.S. Cl.
CPC ............ *A61K 31/12* (2013.01); *A61K 9/0056* (2013.01); *A61K 9/1617* (2013.01); *A61K 9/2009* (2013.01); *A61K 9/2013* (2013.01); *A61K 9/2027* (2013.01); *A61K 9/2054* (2013.01); *A61K 9/4866* (2013.01); *A61K 47/10* (2013.01); *A61K 47/12* (2013.01); *A61K 47/22* (2013.01); *A61K 47/26* (2013.01); *A61K 47/42* (2013.01);

(Continued)

(58) Field of Classification Search
CPC ........ A61K 31/12; A61K 47/10; A61K 47/12; A61K 47/16; A61K 47/22; A61K 47/26; A61K 47/42; A61K 9/0056; A61K 9/145; A61K 9/1617; A61K 9/2009; A61K 9/2013; A61K 9/2027; A61K 9/2054; A61K 9/4866; A61P 5/00; A61P 5/14; A61P 5/02
See application file for complete search history.

(56) References Cited

FOREIGN PATENT DOCUMENTS

WO   WO20070513134   *   5/2007

OTHER PUBLICATIONS

CN 101585757 with translation (Year: 2009).*

* cited by examiner

*Primary Examiner* — Savitha M Rao (57) ABSTRACT

The invention discloses compositions comprising bisdemethoxycurcumin and methods for managing polycystic ovary syndrome (PCOS) and its associated conditions which include hormonal imbalance, obesity, hypothyroidism, hyperandrogenism, oxidative stress, inflammation, gut dysbiosis, hypercholesterolemia, cardiovascular complications, hyperglycemia and insulin resistance. The invention also discloses the potential of a curcuminoid composition comprising 20-80% w/w bisdemethoxycurcumin, 10-35% w/w demethoxycurcumin and 10-50% w/w curcumin for use in the therapeutic management of PCOS.

14 Claims, 4 Drawing Sheets

(51) Int. Cl.
*A61K 47/10* (2017.01)
*A61K 47/12* (2006.01)
*A61K 47/22* (2006.01)
*A61K 47/26* (2006.01)
*A61K 47/42* (2017.01)
*A61P 5/00* (2006.01)
*A61P 5/14* (2006.01)
*A61P 5/24* (2006.01)

(52) U.S. Cl.
CPC .................. *A61P 5/00* (2018.01); *A61P 5/14* (2018.01); *A61P 5/24* (2018.01)

COMPOSITIONS FOR MANAGEMENT OF POLYCYSTIC OVARY SYNDROME

CROSS REFERENCE TO RELATED APPLICATIONS

This application is a non-provisional filing of U.S. provisional application No. 63/182,166, filed on 30 Apr. 2021, the contents of which are incorporated herein by reference

FIELD OF INVENTION

The present invention relates to compositions and methods for managing polycystic ovary syndrome (PCOS). Specifically, the invention relates to the potential of a composition enriched in bisdemethoxycurcumin for the therapeutic management of PCOS. More specifically the invention relates to a curcuminoid composition comprising 20-80% w/w bisdemethoxycurcumin, 10-35% w/w demethoxycurcumin and 10-50% w/w curcumin for use in the therapeutic management of PCOS.

BACKGROUND OF THE INVENTION

Description of Prior Art

Polycystic ovary syndrome (PCOS) is the hormonal disorder affecting 6-18% of women in reproductive age, causing several signs, symptoms and a range of phenotypes, which may include reproductive, endocrine, and metabolic alterations (Rocha et al. Recent advances in the understanding and management of polycystic ovary syndrome, F1000 Faculty Rev, 2019,8, 565). Typically, PCOS is characterized by hyperandrogenism present in 60 to 80% of cases, increased health risk of infertility, miscarriage, pregnancy complications. PCOS also causes metabolic abnormalities that increase their risk of obesity, type 2 diabetes, and cardiovascular disease. In the case of obese patients, (a) insulin resistance and hyperinsulinemia plays a key role compared to non-obese PCOS women, (b) Different hormonal environment compared to normal weight PCOS afflicted women, and it has been shown that weight loss as the best approach for treating obese PCOS women, which improves hyperandrogenism, favors ovulation, and better fertility rate in 25% of women (Gambineri et al. Obesity and the polycystic ovary syndrome, Int. Journal of Obesity 2002, 26, 883-896). Studies have shown that C-reactive protein (CRP) levels, marker for cardio-vascular diseases, and inflammatory cytokines are significantly higher in PCOS patients compared to controls (Zeev Blumenfeld, The Possible Practical Implication of High CRP Levels in PCOS, Clin Med Insights Reprod Health 2019, 13, 1-5). Regarding treatment, improvement of lifestyle forms the first line of attack in combination with many pharmaceutical interventions such as Metformin, GLP-1R agonist, Liraglutide, have shown significant weight loss for PCOS women, which decreases the risk of developing glucose intolerance, type 2 diabetes.

Among the pharmaceutical therapy, Metformin and clomiphene citrate (CC) have been extensively used. It has been shown that Metformin improved insulin resistance in women with PCOS, and decreased circulating androgens. But the therapeutic regimens have not been standardized in clinical practice and most importantly the ability to reduce androgen and improve menses are independence of the doses, indicating further scrutiny. Also, prior treatment of Metformin improved ovulatory response to CC and the combination of these drugs seem to have an improvement in birth rate than individually (Renato, Contemporary approaches to the management of polycystic ovary syndrome, Therapeutic Advances in Endocrinology and Metabolism, 2018, 9(4) 123-134). In regard to the treatment by natural products and its extracts, US 2021/0015883 A1 covers a herbal formulation comprising curcuma lings extract, turmerone oil, Phylanthus emblica juice powder for reducing insulin resistance, and blood glucose levels in diabetic patients, prediabetic condition, diabetes mellitus, insulin resistant diabetes, and polycystic ovarian disorder. Shima et al. have shown inhibitory effects on the expression levels of TNF-α, serum IL-6, and CRP, thereby its effect on PCOS through anti-inflammatory and antioxidant effects of curcumin. In another study by the same group, curcumin exhibited protective effects against inflammation due to PCOS by decreasing liver inflammation through insulin sensitivity and reduction of hepatic necrosis. Jamilian et al. have shown curcumin with beneficial effects on body weight, glycemic control, serum lipids. Abuelezz et al. have studied the role of Nanocurcumin, as means of improving bioavailability, and significantly improved oxidative markers, glucose indices and TNF-α levels and alleviated insulin resistance (Abuelezz et al. Nanocurcumin alleviates insulin resistance and pancreatic deficits in polycystic ovary syndrome rats: Insights on PI3K/AkT/mTOR and TNF-α modulations, 2020, Life Sci. 256(1), 118003).

However, curcumin that is commercially available includes three curcuminoids, 72 to 77% curcumin, 14 to 18% dimethoxy curcumin, and 3 to 5% bis-demethoxy curcumin. And larger fraction of curcumin makes it hydrophobic and thereby affecting bioavailability and absorption (Pushpakumari, K. N et al. Enhancing the Absorption of Curcuminoids from Formulated Turmeric Extracts, 2015; 6(6) 2468-2476). The biological properties of curcumin, bisdemethoxycurcumin and demethoxycurcumin vary in different diseases conditions and recently bisdemethoxycurcumin and demethoxycurcumin are garnering the much attention owing to their similar and superior efficacy over curcumin in managing certain disease conditions. (Majeed et al., Reductive Metabolites of Curcuminoids, Nutriscience Publishers LLC, 2019).

Currently the physician has to choose the appropriate therapeutic approach based on clinical manifestations etc. There is still a void and unmet need for a treatment that is safe, with minimal side effects and yet effective. There exists an unmet industrial need to find a composition that is useful in managing all the associated conditions viz, diabetes, insulin resistance, obesity, hormonal changes, hypothyroidism, gut microbial diversity changes, oxidative stress and inflammation that is associated with PCOS. The present invention solves the above mentioned problem by disclosing a composition enriched in bisdemethoxycurcumin, specifically comprising 20-80% w/w bisdemethoxycurcumin, 10-35% w/w demethoxycurcumin and 10-50% w/w curcumin for the management of PCOS and its associated conditions.

It is the main object of the invention to disclose a composition and method for managing polycystic ovary syndrome and its associated conditions in a mammal using a composition comprising bisdemethoxycurcumin as an active agent.

It is another object of the invention to disclose a composition and method for managing polycystic ovary syndrome in a mammal, wherein the composition comprises 20-80% w/w bisdemethoxycurcumin, 10-35% w/w demethoxycurcumin and 10-50% w/w curcumin.

The present invention fulfils the abovementioned objects and provides further related advantages.

SUMMARY OF THE INVENTION

In a most preferred embodiment, the invention discloses a method for the management of polycystic ovary syndrome and its associated conditions in a mammal, said method comprising steps of a) identifying a female mammalian subject with polycystic ovary syndrome and b) administering an effective dose of bisdemethoxycurcumin to the said subject to alleviate the signs and symptoms of polycystic ovary syndrome.

In another most preferred embodiment, the invention discloses the potential of a composition comprising bisdemethoxycurcumin for use in the management of polycystic ovary syndrome and its associated conditions in a subject.

In another most preferred embodiment, the invention discloses a method for the management of polycystic ovary syndrome and its associated conditions in a subject, said method comprising steps of a) identifying a female mammalian subject with polycystic ovary syndrome and b) administering an effective dose of a composition comprising 20-80% w/w bisdemethoxycurcumin, 10-35% w/w demethoxycurcumin and 10-50% w/w curcumin to the said subject to alleviate the signs and symptoms of polycystic ovary syndrome.

In another most preferred embodiment, the invention discloses a composition comprising 20-80% w/w bisdemethoxycurcumin, 10-35% w/w demethoxycurcumin and 10-50% w/w curcumin for use in the management of polycystic ovary syndrome and its associated conditions in a subject. In a related aspect, the composition comprises of 30-50% w/w bisdemethoxycurcumin, 10-25% w/w demethoxycurcumin and 30-50% w/w curcumin.

Other features and advantages of the present invention will become apparent from the following more detailed description, which illustrate, by way of example, the principle of the invention.

DETAILED DESCRIPTION OF PREFERRED EMBODIMENTS

Definitions of Abbreviations

For clarity, it is stated that percentage in composition comprising 20-80% w/w bisdemethoxycurcumin, 10-35% w/w demethoxycurcumin and 10-50% w/w curcumin is based on the total curcuminoid content.

The following terms can be used alternatively in the specification:
Polycystic ovary syndrome—PCOS
Bisdemethoxycurcumin—BDMC
AC3 complex—composition comprising 20-80% w/w bisdemethoxycurcumin, 10-35% w/w demethoxycurcumin and 10-50% w/w curcumin
Luteinizing hormone—LH
Follicle Stimulating Hormone—FSH
Thyroid stimulating hormone—TSH
Gonadotropin-releasing hormone—GnRH
Receptor for advance glycation end products—RAGE
Paraoxonase-1—PON1
Malondialdehyde—MDA
Advance glycation end products—AGEs In a most preferred embodiment, the invention discloses a method for the management of polycystic ovary syndrome and its associated conditions in a subject, said method comprising steps of a) identifying a female mammalian subject with polycystic ovary syndrome and b) administering an effective dose of bisdemethoxycurcumin to the said subject to alleviate the signs and symptoms of polycystic ovary syndrome, wherein the bisdemethoxycurcumin in formulated along with stabilizing agents, bioavailability enhancers, antioxidants, pharmaceutically or nutraceutically or cosmeceutically accepted excipients, enhancers and administered orally in the form of tablets, capsules, syrups, gummies, powders, suspensions, emulsions, chewables, candies or eatables. In a related aspect, the associated conditions are selected from the group consisting of hormonal imbalance, obesity, hypothyroidism, hyperandrogenism, oxidative stress, inflammation, gut dysbiosis, hypercholesterolemia and cardiovascular complications, hyperglycemia and insulin resistance. In another related aspect, the signs and symptoms of polycystic ovary syndrome are selected from the group consisting irregular periods, polycystic ovary, excessive body hair, weigh gain, Acne or oily skin, Male-pattern baldness or thinning hair, Infertility, skin darkening and skin tags. In another related aspect, hormonal imbalance associated with polycystic ovary syndrome is alleviated by decreasing serum levels of Luteinizing hormone and increasing the levels of 17-β estradiol, Progesterone and Follicle Stimulating Hormone. In yet another related aspect, obesity associated with polycystic ovary syndrome is managed by decreasing body weight, ovarian weight and increasing the expression of serum adiponectin. In yet another related aspect, hypothyroidism associated with polycystic ovary syndrome is managed by decreasing the levels of thyroid stimulating hormone and increasing the serum levels of T3 and T4. In yet another related aspect, hyperandrogenism associated with polycystic ovary syndrome is managed by decreasing the expression of serum testosterone. In yet another related aspect, hyperglycemia and insulin resistance associated with polycystic ovary syndrome is managed by increasing the levels of serum Omentin-1. In yet another related aspect, gut dysbiosis associated with polycystic ovary syndrome is managed by increasing Ghrelin levels in the serum. In yet another related aspect, hypercholesterolemia and cardiovascular complications associated with polycystic ovary syndrome is managed by increasing Paraoxonase-1 levels in the serum. In yet another related aspect, oxidative stress associated with polycystic ovary syndrome is reduced by decreasing serum malondialdehyde levels. In yet another related aspect, inflammation associated with polycystic ovary syndrome is reduced by decreasing the levels of advance glycation end products (AGE). In another related aspect, the effective dose of bisdemethoxycurcumin is 25-50 mg/kg bodyweight. In a preferred aspect, the subject is a mammalian female.

In another most preferred embodiment, the invention discloses the potential of a composition comprising bisdemethoxycurcumin for use in the management of polycystic ovary syndrome and its associated conditions in a subject, wherein the bisdemethoxycurcumin in formulated along with stabilizing agents, bioavailability enhancers, antioxidants, pharmaceutically or nutraceutically or cosmeceutically accepted excipients, enhancers and administered orally in the form of tablets, capsules, syrups, gummies, powders, suspensions, emulsions, chewables, candies or eatables. In a related aspect, the associated conditions are selected from the group consisting of hormonal imbalance, obesity, hypothyroidism, hyperandrogenism, oxidative stress, inflammation, gut dysbiosis, hypercholesterolemia and cardiovascular complications, hyperglycemia and insulin resistance. In another related aspect, the signs and symptoms of polycystic ovary syndrome are selected from the group consisting irregular periods, polycystic ovary, excessive body hair, weigh gain, Acne or oily skin, Male-pattern baldness or thinning hair, Infertility, skin darkening and skin tags. In another related aspect, hormonal imbalance associated with polycystic ovary syndrome is alleviated by decreasing serum levels of Luteinizing hormone and increasing the levels of 17-β estradiol, Progesterone and Follicle Stimulating Hormone. In yet another related aspect, obesity associated with polycystic ovary syndrome is managed by decreasing body weight, ovarian weight and increasing the expression of serum adiponectin. In yet another related aspect, hypothyroidism associated with polycystic ovary syndrome is managed by decreasing the levels of thyroid stimulating hormone and increasing the serum levels of T3 and T4. In yet another related aspect, hyperandrogenism associated with polycystic ovary syndrome is managed by decreasing the expression of serum testosterone. In yet another related aspect, hyperglycemia and insulin resistance associated with polycystic ovary syndrome is managed by increasing the levels of serum Omentin-1. In yet another related aspect, gut dysbiosis associated with polycystic ovary syndrome is managed by increasing Ghrelin levels in the serum. In yet another related aspect, hypercholesterolemia and cardiovascular complications associated with polycystic ovary syndrome is managed by increasing Paraoxonase-1 levels in the serum. In yet another related aspect, oxidative stress associated with polycystic ovary syndrome is reduced by decreasing serum malondialdehyde levels. In yet another related aspect, inflammation associated with polycystic ovary syndrome is reduced by decreasing the levels of advance glycation end products (AGE). In another related aspect, the effective dose of bisdemethoxycurcumin is 25-50 mg/kg bodyweight. In a preferred aspect, the subject is a mammalian female.

In another most preferred embodiment, the invention discloses a method for the management of polycystic ovary syndrome and its associated conditions in a subject, said method comprising steps of a) identifying a female mammalian subject with polycystic ovary syndrome and b) administering an effective dose of a composition comprising 20-80% w/w bisdemethoxycurcumin, 10-35% w/w demethoxycurcumin and 10-50% w/w curcumin to the said subject to alleviate the signs and symptoms of polycystic ovary syndrome. In a related aspect, the composition comprises of 30-50% w/w bisdemethoxycurcumin, 10-25% w/w demethoxycurcumin and 30-50% w/w curcumin. In yet another related aspect, the total curcuminoids in the composition are in the range of 20-95% w/w. In a related aspect, the associated conditions are selected from the group consisting of hormonal imbalance, obesity, hypothyroidism, hyperandrogenism, oxidative stress, inflammation, gut dysbiosis, hypercholesterolemia and cardiovascular complications, hyperglycemia and insulin resistance. In another related aspect, the signs and symptoms of polycystic ovary syndrome are selected from the group consisting irregular periods, polycystic ovary, excessive body hair, weigh gain, Acne or oily skin, Male-pattern baldness or thinning hair, Infertility, skin darkening and skin tags. In another related aspect, hormonal imbalance associated with polycystic ovary syndrome is alleviated by decreasing serum levels of Luteinizing hormone and increasing the levels of 17-β estradiol, Progesterone and Follicle Stimulating Hormone. In yet another related aspect, obesity associated with polycystic ovary syndrome is managed by decreasing body weight, ovarian weight and increasing the expression of serum adiponectin. In yet another related aspect, hypothyroidism associated with polycystic ovary syndrome is managed by decreasing the levels of thyroid stimulating hormone and increasing the serum levels of T3 and T4. In yet another related aspect, hyperandrogenism associated with polycystic ovary syndrome is managed by decreasing the expression of serum testosterone. In yet another related aspect, hyperglycemia and insulin resistance associated with polycystic ovary syndrome is managed by increasing the levels of serum Omentin-1. In yet another related aspect, gut dysbiosis associated with polycystic ovary syndrome is managed by increasing Ghrelin levels in the serum. In yet another related aspect, hypercholesterolemia and cardiovascular complications associated with polycystic ovary syndrome is managed by increasing Paraoxonase-1 levels in the serum. In yet another related aspect, oxidative stress associated with polycystic ovary syndrome is reduced by decreasing serum malondialdehyde levels. In yet another related aspect, inflammation associated with polycystic ovary syndrome is reduced by decreasing the levels of advance glycation end products (AGE). In another related aspect, the effective dose of composition is 100-200 mg/kg bodyweight. In a preferred aspect, the subject is a mammalian female. In another related aspect, the composition is formulated with stabilizing agents, bioavailability enhancers, antioxidants, pharmaceutically or nutraceutically or cosmeceutically accepted excipients, enhancers and administered orally in the form of tablets, capsules, syrups, gummies, powders, suspensions, emulsions, chewables, candies or eatables.

In another most preferred embodiment, the invention discloses a composition comprising 20-80% w/w bisdemethoxycurcumin, 10-35% w/w demethoxycurcumin and 10-50% w/w curcumin for use in the management of polycystic ovary syndrome and its associated conditions in a subject. In a related aspect, the composition comprises of 30-50% w/w bisdemethoxycurcumin, 10-25% w/w demethoxycurcumin and 30-50% w/w curcumin. In yet another related aspect, the total curcuminoids in the composition are in the range of 20-95% w/w. In a related aspect, the associated conditions are selected from the group consisting of hormonal imbalance, obesity, hypothyroidism, hyperandrogenism, oxidative stress, inflammation, gut dysbiosis, hypercholesterolemia and cardiovascular complications, hyperglycemia and insulin resistance. In another related aspect, the signs and symptoms of polycystic ovary syndrome are selected from the group consisting irregular periods, polycystic ovary, excessive body hair, weigh gain, Acne or oily skin, Male-pattern baldness or thinning hair, Infertility, skin darkening and skin tags. In another related aspect, hormonal imbalance associated with polycystic ovary syndrome is alleviated by decreasing serum levels of Luteinizing hormone and increasing the levels of 17-β estradiol, Progesterone and Follicle Stimulating Hormone. In yet another related aspect, obesity associated with polycystic ovary syndrome is managed by decreasing body weight, ovarian weight and increasing the expression of serum adiponectin. In yet another related aspect, hypothyroidism associated with polycystic ovary syndrome is managed by decreasing the levels of thyroid stimulating hormone and increasing the serum levels of T3 and T4. In yet another related aspect, hyperandrogenism associated with polycystic ovary syndrome is managed by decreasing the expression of serum testosterone. In yet another related aspect, hyperglycemia and insulin resistance associated with polycystic ovary syndrome is managed by increasing the levels of serum Omentin-1. In yet another related aspect, gut dysbiosis associated with polycystic ovary syndrome is managed by increasing Ghrelin levels in the serum. In yet another related aspect, hypercholesterolemia and cardiovascular complications associated with polycystic ovary syndrome is managed by increasing Paraoxonase-1 levels in the serum. In yet another related aspect, oxidative stress associated with polycystic ovary syndrome is reduced by decreasing serum malondialdehyde levels. In yet another related aspect, inflammation associated with polycystic ovary syndrome is reduced by decreasing the levels of advance glycation end products (AGE). In another related aspect, the effective dose of the composition is 100-200 mg/kg bodyweight. In a preferred aspect, the subject is a mammalian female. In another related aspect, the composition is formulated with stabilizing agents, bioavailability enhancers, antioxidants, pharmaceutically or nutraceutically or cosmeceutically accepted excipients, enhancers and administered orally in the form of tablets, capsules, syrups, gummies, powders, suspensions, emulsions, chewables, candies or eatables.

In yet another related embodiment the bioavailability enhancer is selected from the group consisting of, but not limited to, piperine, quercetin, garlic extract, ginger extract, and naringin.

In another related aspect, one or more anti-oxidants and anti-inflammatory agents are selected from the group consisting of, but not limited to, vitamin A, D, E, K, C, B complex, rosmarinic acid, Alpha Lipoic Acid, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosylrutin, catalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

Specific illustrative examples enunciating the most preferred embodiments are included herein below.

EXAMPLES

Example 1: Composition

The bisdemethoxycurcumin can be isolated from *Curcuma longa* and also chemically synthesised. The sample of bisdemethoxycurcumin used in the invention was sourced from Sami-Sabinsa Group limited, Bangalore, India. The composition comprising 20-80% w/w bisdemethoxycurcumin, 10-35% w/w demethoxycurcumin and 10-50% w/w curcumin was isolated from a selected variety of *Curcuma longa* as per the procedure disclosed in U.S. patent application Ser. No. 17/644,990 which is incorporated herein by reference Example 2— Management of PCOS and Associated Conditions In the present invention the potential of a composition comprising 20-80% w/w bisdemethoxycurcumin, 10-35% w/w demethoxycurcumin and 10-50% w/w curcumin (AC3 complex), preferably in the range of 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin) was tested for its potential in the management of PCOS. It is to be noted that the range tested is merely illustrative and the results are application to the aforementioned ranges of the composition.

Animals and Experimental design: Animals were housed under standard air-conditioned laboratory conditions. The temperature was maintained at maximum: 24° C. and a minimum of 23° C. and Relative humidity at maximum: 63% and a minimum of 48% with 12 h light and 12 h dark cycle. The maximum and minimum temperature and relative humidity in the experimental room were recorded once daily. Female virgin Wistar rats (150-200 g) was checked daily for 4-day ovarian cycle using vaginal cytology. PCOS was induced by oral administration of aromatase inhibitor, letrozole (1 mg/kg) dissolved in 0.5% CMC (2 mg/kg) for 21 days. During the experiment, the estrous cycle was monitored by the analyses of relative proportion of leukocytes, epithelial and cornified cells in vaginal smears.

Following letrozole administration, test samples were administered to animals from day 22 to day 36. After treatment protocol, animal from all groups (Table 1) were fasted overnight and anesthetized with diethylether/halothane. The blood was collected by retino-orbital puncture, then serum was separated by centrifugation followed by estimation of hormones and other biochemical parameters using commercially available ELISA kits.

TABLE 1

| Groups | |
|---|---|
| Groups | Description |
| Group 1 | Normal Control |
| Group 2 | PCOD Control |
| Group 3 | BDMC 3.12 mg/kg |
| Group 4 | BDMC 6.25 mg/kg |
| Group 5 | BDMC 12.5 mg/kg |
| Group 6 | BDMC 25 mg/kg |
| Group 7 | BDMC 50 mg/kg |
| Group 8 | AC3 complex 12.5 mg/kg |
| Group 9 | AC3 complex 25 mg/kg |
| Group 10 | AC3 complex 50 mg/kg |
| Group 11 | AC3 complex 100 mg/kg |
| Group 12 | AC3 complex 200 mg/kg |

Parameters Analysed for Selecting the Effective Dose:

The serum hormone levels, body weight and ovary weigh of the animals were assessed to ascertain the effective dose.

PCOS is an endocrine disorder wherein it affects the normal release and function of variety of hormones. Generally, Gonadotropin-releasing hormone (GnRH) is responsible for the normal release of LH and FSH from the pituitary gland. In females, LH controls the menstrual cycle and in males it is responsible for the release of testosterone. FSH on the other hand helps is controlling the menstrual cycle and stimulates the growth of eggs in the ovaries. In PCOS, the brain does not produce GnRHin normal cycles, causing the LH levels to rise and FSH levels to drop. The increase LH causes ovaries to produce more testosterone which promotes the appearance of male like features in a woman. Due to the lack of FSH, the ovaries are unable to produce egg leading to infertility (Leo et al., Genetic, hormonal and metabolic aspects of PCOS: an update, Reproductive Biology and Endocrinology (2016) 14:38, DOI 10.1186/s12958-016-0173-x).

In the present study, administration of Letrozole, 1 mg/kg, p. o. increased the levels of LH and decreased the FSH levels. The levels of 17-$\beta$ estradiol, which is responsible for the development of female secondary sexual characters and regulation of menstrual cycle also decreased significantly. Progesterone levels were also decreased signifying disturbance in the normal menstrual cycle. BDMC at 25 mg/kg and AC3 complex at 100 mg/kg was effective in reversing the hormonal disturbances in PCOS (Table 2)

TABLE 2

Serum hormonal levels in PCOS

| Treatment group | Serum hormonal levels | | | |
|---|---|---|---|---|
| | 17-$\beta$ estradiol (pg/mL) | Progesterone (ng/ml) | FSH (mIU/mL) | LH (mIU/mL) |
| Normal control | 23.42 ± 1.33 | 28.52 ± 1.42 | 16.54 ± 1.06 | 20.32 ± 1.21 |
| PCOS control (Letrozole, 1 mg/kg, p.o.) | 12.34 ± 2.46 | 17.43 ± 1.30 | 9.57 ± 1.23 | 29.65 ± 2.05 |
| BDMC 3.12 mg/kg | 16.89 ± 3.01 | 18.67 ± 1.03 | 10.54 ± 1.44 | 26.33 ± 3.02 |
| BDMC 6.25 mg/kg | 18.22 ± 2.44* | 20.56 ± 1.09 | 10.98 ± 1.52 | 27.32 ± 2.30 |
| BDMC 12.5 mg/kg | 18.89 ± 1.65* | 23.50 ± 2.21* | 12.58 ± 1.08* | 24.36 ± 2.11 |
| BDMC 25 mg/kg | 22.50 ± 1.67** | 26.95 ± 1.53** | 13.28 ± 1.34* | 21.54 ± 1.26** |
| BDMC 50 mg/kg | 21.26 ± 2.32** | 26.28 ± 1.22** | 13.07 ± 1.36** | 22.78 ± 1.76* |
| AC3 Complex 12.5 mg/kg | 15.67 ± 3.85 | 19.44 ± 1.15 | 10.81 ± 2.46 | 27.05 ± 2.22 |
| AC3 Complex 25 mg/kg | 19.21 ± 3.62* | 20.75 ± 2.37 | 12.73 ± 1.98 | 26.11 ± 2.63 |
| AC3 Complex 50 mg/kg | 19.53 ± 2.49* | 22.93 ± 4.01* | 13.35 ± 3.87* | 23.99 ± 3.01 |
| AC3 Complex 100 mg/kg | 21.49 ± 3.44** | 25.82 ± 2.88** | 14.66 ± 2.01** | 23.04 ± 1.28* |
| AC3 Complex 200 mg/kg | 22.02 ± 2.27** | 25.01 ± 1.66** | 13.27 ± 1.83* | 24.58 ± 3.04 |

*$p < 0.01$,
**$p < 0.001$

Obesity is one of the common features that is associated with PCOS. Due to the hormonal imbalance, insulin resistance occurs thereby leading to the build up of glucose in the blood (hyperglycemia). Insulin resistance also indues the release of male hormones which triggers weight gain, specifically the deposition of fat in the abdomen (Sam et al., Obesity and Polycystic Ovary Syndrome, Obes Manag. 2007 April; 3(2): 69-73. doi:10.1089/obe.2007.0019).

In the present study, Letrozole, 1 mg/kg, p. o. significantly increased the body weight (Table 3) and ovary weight (Table 4).

TABLE 3

Body weight in PCOS

| Treatment | Average body weight (g) | | | | | |
|---|---|---|---|---|---|---|
| | PCOS induction | | | | PCOS + Treatment | |
| | Day 1 | Day 7 | Day 14 | Day 21 | Day 28 | Day 36 |
| Normal control | 157 ± 3.15 | 171 ± 5.01 | 182.5 ± 2.5 | 190 ± 5.74 | 202.5 ± 6.5 | 210 ± 5.42 |
| PCOS control (Letrozole, 1 mg/kg. p.o.) | 158 ± 4.17 | 174 ± 6.65 | 187 ± 8.15 | 215 ± 7.34 | 226 ± 8.16 | 235 ± 6.54 |

TABLE 3-continued

Body weight in PCOS

| | Average body weight (g) | | | | | |
|---|---|---|---|---|---|---|
| | PCOS induction | | | | PCOS + Treatment | |
| Treatment | Day 1 | Day 7 | Day 14 | Day 21 | Day 28 | Day 36 |
| BDMC 3.12 mg/kg | 158 ± 6.16 | 175 ± 5.27 | 194 ± 5.77 | 210 ± 7.58 | 202 ± 4.15 | 200 ± 6.36 |
| BDMC 6.25 mg/kg | 157 ± 8.15 | 175.3 ± 4.5 | 195.5 ± 6.6 | 215 ± 5.78 | 201 ± 6.88 | 198 ± 6.45 |
| BDMC 12.5 mg/kg | 158 ± 7.88 | 174 ± 2.83 | 202.5 ± 8.12 | 212 ± 6.36 | 200 ± 6.57 | 196 ± 5.26* |
| BDMC 25 mg/kg | 157.5 ± 8.16 | 172 ± 6.46 | 190.5 ± 4.44 | 210 ± 5.12 | 201 ± 5.54 | 191 ± 5.84** |
| BDMC 50 mg/kg | 157 ± 6.13 | 168 ± 5.47 | 190 ± 10.42 | 211 ± 7.58 | 199 ± 8.15 | 192 ± 6.36** |
| AC3 Complex 12.5 mg/kg | 159 ± 4.72 | 179 ± 4.44 | 200 ± 7.66 | 209 ± 6.39 | 205 ± 2.22 | 202 ± 3.55 |
| AC3 Complex 25 mg/kg | 158 ± 5.47 | 175 ± 6.73 | 202 ± 3.98 | 213 ± 4.28 | 208 ± 4.15 | 201 ± 7.81 |
| AC3 Complex 50 mg/kg | 158 ± 3.86 | 176 ± 5.87 | 203 ± 4.22 | 211 ± 6.73 | 209 ± 5.28 | 202 ± 4.66 |
| AC3 Complex 100 mg/kg | 159 ± 6.59 | 174 ± 7.22 | 200 ± 5.12 | 209 ± 7.31 | 203 ± 4.37 | 199 ± 8.24* |
| AC3 Complex 200 mg/kg | 159 ± 5.89 | 173 ± 6.39 | 204 ± 4.58 | 210 ± 4.68 | 205 ± 4.29 | 199 ± 7.65* |

*p < 0.01,
**p < 0.001

TABLE 4

Body weight in PCOS

| Treatment | Ovarian weight (mg) |
|---|---|
| Normal control | 41.26 ± 1.24 |
| PCOS control (Letrozole, 1 mg/kg, p.o.) | 85.12 ± 3.15 |
| BDMC 3.12 mg/kg | 63.88 ± 2.19 |
| BDMC 6.25 mg/kg | 59.64 ± 2.32* |
| BDMC 12.5 mg/kg | 54.36 ± 2.80* |
| BDMC 25 mg/kg | 47.88 ± 2.76** |
| BDMC 50 mg/kg | 48.54 ± 2.42** |
| AC3 Complex 12.5 mg/kg | 72.99 ± 3.46 |
| AC3 Complex 25 mg/kg | 61.39 ± 3.04 |
| AC3 Complex 50 mg/kg | 58.03 ± 4.79* |
| AC3 Complex 100 mg/kg | 54.22 ± 5.27** |
| AC3 Complex 200 mg/kg | 53.35 ± 3.08** |

*p < 0.01,
**p < 0.001

BDMC at 25 mg/kg and AC3 complex at 100 mg/kg was effective in reducing the body weight and ovarian weight in PCOS.

Based on the above results, the following groups were taken for further analysis BDMC 25 mg/kg p.o.
  BDMC 50 mg/kg p.o.
  AC3 100 mg/kg p.o.
  AC3 200 mg/kg p.o.
  The following molecular targets were assessed:
  1. Thyroid Function analysis
  2. Effect on androgen profile
  3. Effect on serum adiponectin levels
  4. Insulin resistance
  5. Effect on Serum Paraoxonase 1 Activity
  6. Effect of gut microbiota
  7. Oxidative stress and inflammatory markers Thyroid Function Analysis Hypothyroidism is more common in people with PCOS than in the general population. A 2013 study from India found that 22.5% of women with PCOS had hypothyroidism compared to 8.75% of those without PCOS (Sinha et al., Thyroid disorders in polycystic ovarian syndrome subjects: A tertiary hospital based cross-sectional study from Eastern India, Indian J Endocrinol Metab. 2013 Mar.; 17(2):304-9. doi: 10.4103/2230-8210.109714). Hypothyroidism is known to affect the ovaries in a similar way as PCOS, causing the enlargement of the ovaries and the formation of cysts. Hypothyroidism can worsen the symptoms of PCOS, including increased insulin resistance, irregular periods, abnormal hair growth, and male-pattern baldness. It can also affect ovulation and the normal development of eggs (Singla et al., Thyroid disorders and polycystic ovary syndrome: An emerging relationship Indian J Endocrinol Metab. 2015; 19(1):25-29. doi:10.4103/2230-8210.146860).

In PCOS, rise in thyrotropin-releasing hormone (TRH) in primary hypothyroidism leads to increased prolactin (PRL) and thyroid stimulating hormone (TSH). Prolactin contributes toward polycystic ovarian morphology by inhibiting ovulation as a result of the change in the ratio of follicle stimulating hormone (FSH) and luteinizing hormone (LH) (Singla et al., Thyroid disorders and polycystic ovary syndrome: An emerging relationship Indian J Endocrinol Metab. 2015; 19(1):25-29. doi:10.4103/2230-8210.146860).

In the present investigation, the levels of T3 and T4 were significantly lowered in PCOS and the TSH levels were elevated (Table 5).

TABLE 5

Thyroid hormone levels in PCOS

| Group | Treatment group | Serum hormonal levels | | |
|---|---|---|---|---|
| | | T3 (µIU/ml) | T4 (µIU/ml) | TSH (nmol/L) |
| I | Normal control | 3.6 ± 0.21 | 12.76 ± 0.29 | 1.75 |
| II | PCOS control (Letrozole, 1 mg/kg, p.o.) | 0.27 ± 0.03 | 2.29 ± 0.20 | 16.83 |
| III | BDMC 25 mg/kg | 3.3 ± 0.18** | 11.78 ± 0.39** | 5.28** |
| IV | BDMC 50 mg/kg | 3.05 ± 0.17** | 10.45 ± 0.27** | 7.12** |
| V | AC3 Complex 100 mg/kg | 2.15 ± 0.32** | 8.23 ± 0.34** | 9.52** |
| VI | AC3 Complex 200 mg/kg | 2.22 ± 0.54** | 6.77 ± 0.93* | 10.43* |

*p < 0.01,
**p < 0.001

Elevated TSH and lower T3 and T4 levels (Hypothyroidism) are commonly associated with PCOS and there is a need to examine and correct the hypothyroidism in women with PCOS (Trummer et al., Impact of elevated thyroid-stimulating hormone levels in polycystic ovary syndrome, Gynecological Endocrinology, 2015; 31:10, 819-823, DOI: 10.3109/09513590.2015.1062864). Bisdemethoxycurcmin at both 25 and 50 mg/kg and AC3 complex at 100 and 200 mg/kg bodyweight effective in reversing the imbalance in the levels of thyroid hormones and correcting hypothyroidism.

Effect on Androgen Profile

Hyperandrogenism is the defining feature of women with PCOS. It is caused by the disruption of normal ovarian or adrenal function resulting in the production of excess androgens. The first impact of androgen excess in PCOS is impaired folliculogenesis. Androgens may increase in women with PCOS because of the high levels of LH but also because of increased levels of insulin that are usually seen with PCOS (Paris et al., The Mechanism of Androgen Actions in PCOS Etiology, Med. Sci. 2019, 7, 89; doi: 10.3390/medsci7090089).

Figure 1:
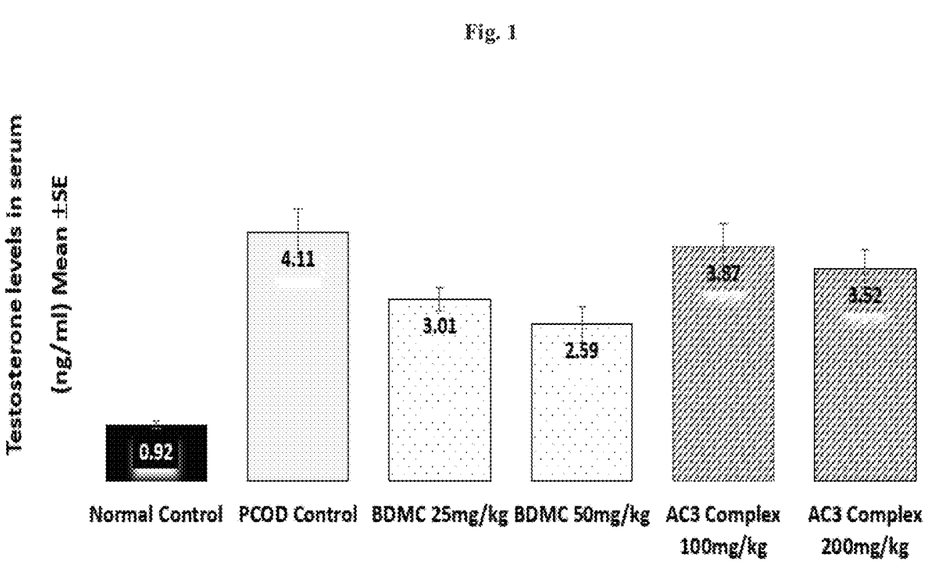
FIG. 1 shows measure of Testosterone levels in serum for normal, PCOD control. BDMC (25 and 50 mg/kg), and AC3 complex (100 and 200 mg/kg). *p<0.01.

In the current investigation, the testosterone levels in mice with PCOS were increased significantly which is lowered with the administration of both BDMC and AC3 complex (FIG. 1)

Effect on Serum Adiponectin Levels

Figure 2:
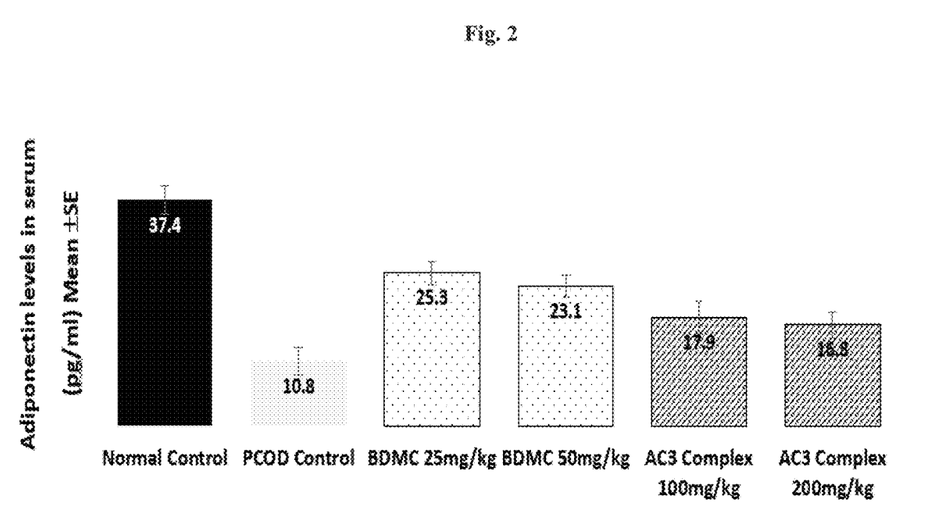
FIG. 2 shows measure of Adiponectin levels in serum for normal, PCOD control. BDMC (25 and 50 mg/kg), and AC3 complex (100 and 200 mg/kg). *p<0.001

Obesity is one of the features that is generally associated with PCOS. There are many factors for the development of obesity. The relationships between adiponectin, insulin resistance and sensitivity, metabolic syndrome, and BMI in women with PCOS suggest that adiponectin serves as a potential marker for disease risk (Glintborg, D et al.(2006). Evaluation of metabolic risk markers in polycystic ovary syndrome (PCOS). Adiponectin, ghrelin, leptin and body composition in hirsute PCOS patients and controls, European Journal of Endocrinology, 155(2), 337-345). Obese, PCOS patients generally exhibit lower adiponectin levels than obese controls, which is also reported in the present study (FIG. 2). Both BDMC and AC3 complex were effective in reducing increasing the adiponectin levels and thus is an effective molecule/composition for the management of obesity in women with PCOS.

Insulin Resistance

Figure 3:
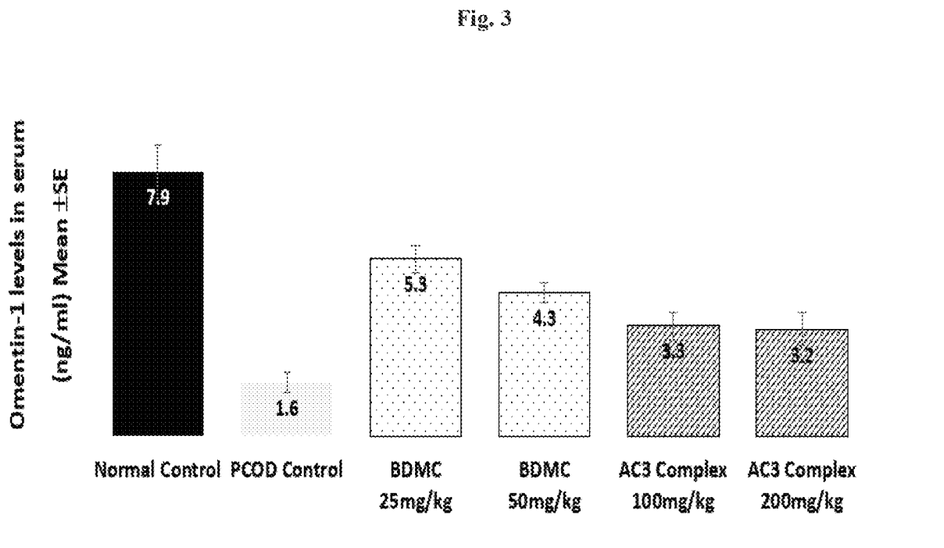
FIG. 3 shows measure of Omentin-1 levels in serum for normal, PCOD control. BDMC (25 and 50 mg/kg), and AC3 complex (100 and 200 mg/kg). *p<0.01**p<0.001

Due to the hormonal changes in PCOS, insulin resistance occurs in women with PCOS. There are many adipokines that are involved in regulating the insulin sensitivity and also have been suggested to play an important role in the pathogenesis of PCOS. Omentin-1 is an adipokine secreted essentially by visceral adipose tissue and its circulating levels are correlated with many disease conditions such as insulin resistance, chronic inflammatory conditions, obesity, diabetes and cardiovascular diseases (CVDs), which are risk factors for the development of PCOS (Tang et al., Circulating omentin-1 levels in women with polycystic ovary syndrome: a meta-analysis, Gynecological Endocrinology, 2017; 33:3, 244-249, DOI: 10.1080/09513590.2016.1254180). Suppressed omentin-1 levels in PCOS indicate increased insulin resistance. In the present study the circulating levels of Omentin-1 was lower in PCOS which was increased with the administration of BDMC and AC3 complex (FIG. 3)

The normalization of Omentin-1 levels indicate decrease in insulin resistance which is one of effective ways to manage diabetes and hyperglycemia related to PCOS.

Effect on Serum Paraoxonase 1 Activity

Figure 4:
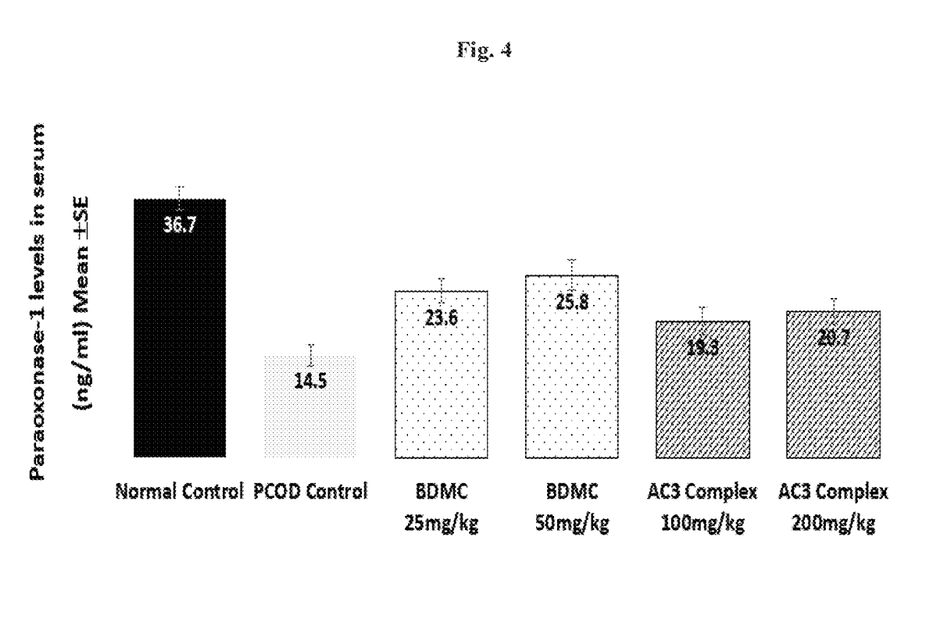
FIG. 4 shows measure of Paraoxonase-1 levels in serum for normal, PCOD control. BDMC (25 and 50 mg/kg), and AC3 complex (100 and 200 mg/kg). *p<0.01**p<0.001.

Paraoxonase-1 (PON1) is an esterase and lactonase synthesized by the liver and found in the circulation associated with high-density lipoproteins. Serum PON1 is located on HDL-cholesterol and is responsible for the antioxidant activity of HDL. Because oxidative stress may impair insulin action, reduced serum paraoxonase activity contributes to insulin resistance in PCOS. Lower levels of PON1, combined with polymorphisms in the PON1 gene increase the risk factor for the development of insulin resistance, elevated cholesterol, cardiovascular complications along with increased oxidative stress (Dursun et al., Decreased serum paraoxonase 1 (PON1) activity: an additional risk factor for atherosclerotic heart disease in patients with PCOS'?, Human Reproduction, Volume 21, Issue 1, January 2006, Pages 104-108, https://doi.org/10.1093/humrep/dei284). In the current study, PON1 levels were observed to be significantly less in PCOS and administration of BDMC (25 and 50 mg/kg bodyweight) and AC3 complex (100 and 200 mg/kg bodyweight) increased the circulating levels of PON1 (FIG. 4). Thus, both BDMC and AC3 complex are effective in managing insulin resistance, hypercholesterolemia and cardiovascular complication resulting from PCOS.

Effect on Gut Microbiota

Gut microbiota plays a major role by influencing physiology, metabolism, nutrition, immune function and the delicate balance between the latter and the host prevents the development of different diseases. There is alteration in the general composition of the microbiome in PCOS and imbalance of some species of bacteria, like Bacteroidetes and Firmicutes. This modification can lead to altered production of short-chain fatty acids with a negative impact on metabolism, gut barrier integrity, and immunity (Giampaolino, et al. Microbiome and PCOS: State-of-Art and Future Aspects. Int. J. Mol. Sci. 2021, 22, 2048). Regarding the genera

Figure 5:
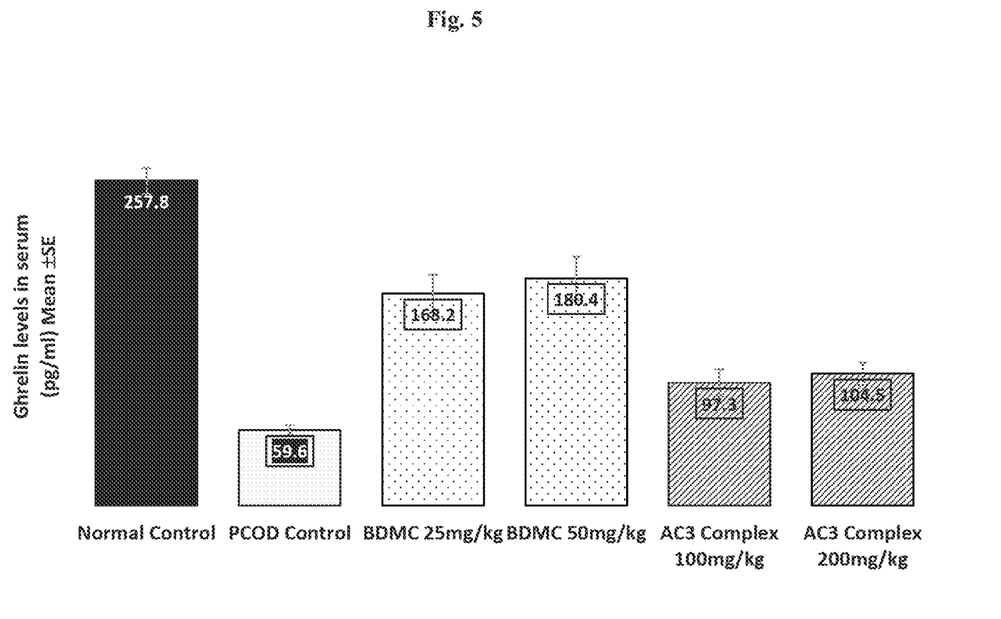
FIG. 5 shows measure of Ghrelin levels in serum for normal, PCOD control. BDMC (25 and 50 mg/kg), and AC3 complex (100 and 200 mg/kg). *p<0.01**p<0.001.

*Bacteroides*, Liu et al. (Dysbiosis of Gut Microbiota Associated with Clinical Parameters in Polycystic Ovary Syndrome. Front. Microbiol. 2017, 8, 324) have observed a specific increase of *Escherichia* and *Shigella* in women with PCOS and reported a lower level of ghrelin and Peptide YY in women with PCOS compared with those of healthy women, due to an increase in *Bacteroides* species that are negatively correlated with ghrelin. Thus, lower levels of ghrelin indicate an increase in *Bacteroides* species and gut dysbiosis. The instant invention also observed a lower ghrelin levels in the PCOS group which, on administration with BDMC/AC3 complex increased significantly (FIG. 5) indicating the fact that both BDMC and AC3 complex are effective in managing gut dysbiosis in PCOS.

Oxidative Stress and Inflammatory Markers

Investigations have revealed that oxidative stress is significantly increased in patients with PCOS. Oxidative stress is significantly correlated with obesity, insulin resistance, hyperandrogenemia, and chronic inflammation and plays pivotal roles in cancer pathogenesis.

Figure 6:
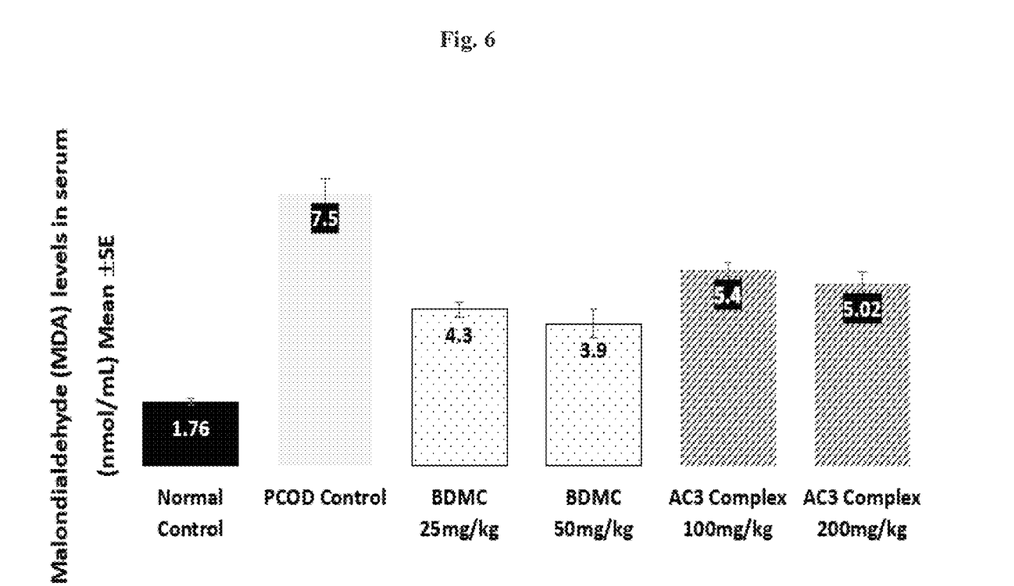
FIG. 6 shows measure of Malondialdehyde levels in serum for normal, PCOD control. BDMC (25 and 50 mg/kg), and AC3 complex (100 and 200 mg/kg)*p<0.01.

Reactive oxygen species (ROS) causes genetic changes by attacking DNA, such as DNA strand breaks, point mutations, aberrant DNA cross-linking, and DNA-protein cross-linking becoming one of the major underlying inducements of the increasing risk of gynecological cancers in PCOS patients. Current employed circulating markers majorly include homocysteine, malondialdehyde (MDA), asymmetric dimethylarginine (AMDA), superoxide dismutase (SOD), glutathione (GSH), and paraoxonase-1 (PON1). Malondialdehyde levels indicate the degree of lipid peroxidation of the cell membranes. The current study also showed that the MDA levels were significantly elevated in the PCOS group which is reduced by the administration of BDMC and AC3 complex (FIG. 6)

Figure 7:
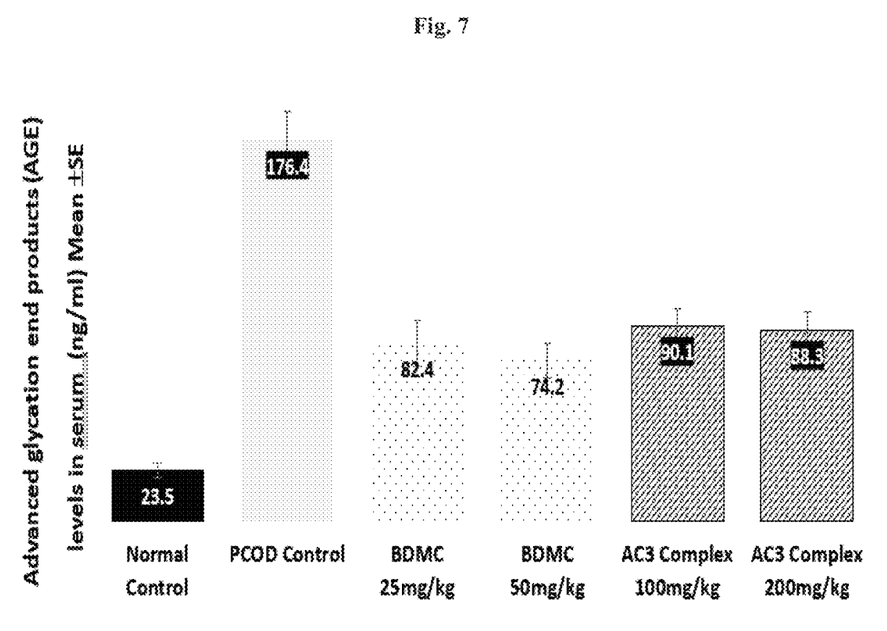
FIG. 7 shows measure of advanced glycation end products (AGE) levels in serum for normal, PCOD control. BDMC (25 and 50 mg/kg), and AC3 complex (100 and 200 mg/kg)*p<0.01.

Reports have shown that advance glycation end products (AGEs) circulating levels and expression of their pro-inflammatory receptors in the ovarian tissue called as receptor for advanced glycation end products (RAGE) are elevated in women with PCOS. Dietary AGEs have similar cell activating and cell oxidative capabilities as endogenous AGEs thus inducing inflammatory signals and promoting oxidative stress and inflammation. Accumulation of dietary AGEs in the tissues further enhances cellular damage via production of reactive oxygen species. In the present study the circulating AGEs were significantly elevated in PCOS group which is decreased by the administration of BDMC and AC3 complex (FIG. 7)

Overall, both BDMC (25 and 50 mg/kg bodyweight) and AC3 complex (100 and 200 mg/kg bodyweight), corresponding to human doses—BDMC—200 mg/day and AC3 complex—800 mg/day, was effective in managing PCOS and its associated conditions which include hormonal imbalance, obesity, hypothyroidism, hyperandrogenism, oxidative stress, inflammation, gut dysbios is, hypercholesterolemia and cardiovascular complications, hyperglycemia and insulin resistance.

Example 3: Formulations Containing BDMC

The composition is formulated along with pharmaceutically/nutraceutically acceptable excipients, adjuvants, diluents, stabilizing agents, dispersible gums, bioavailability enhancers or carriers and administered orally in the form of tablets, capsules, syrups, gummies, powders, suspensions, emulsions, chewables, candies or eatables.

In a related aspect the bioavailability enhancer is selected from the group of piperine (BioPerine®)), quercetin, garlic extract, ginger extract, and naringin. In another related aspect, the stabilizing agent is selected from the group consisting rosmarinic acid, butylated hydroxyanisole, butylated hydroxytoluene, sodium metabisulfite, propyl gallate, cysteine, ascorbic acid and tocopherols. In yet another related aspect, the dispersible gums are selected from the group consisting of Agar, Alginate, Carrageenan, Gum Arabic, Guar Gum, Locust Bean Gum, Konjac Gum, Xanthan Gum and Pectin.

Tables 6-17 provide illustrative examples of nutraceutical formulations containing bisdemethoxycurcumin

TABLE 6

Tablet

Active Ingredients
AC3 complex (Curcumin BD3 Complex)
Excipients
Microcrystalline cellulose, Colloidal silicon dioxide,
Magnesium stearate, BioPerine ®,
Polyvinylpyrrolidone/starch/Hydroxy propyl methyl
cellulose, Hydroxy propyl cellulose

TABLE 7

Capsule

Active Ingredients
AC3 complex (Curcumin BD3 Complex)
Excipients
Microcrystalline cellulose, BioPerine ®

TABLE 8

Powder

Active Ingredients
AC3 complex (Curcumin BD3 Complex)
Excipients
BioPerine ®,

TABLE 9

Gummy formulation

Active Ingredients
AC3 complex (Curcumin BD3 Complex)
Excipients
BioPerine ®, Gelatin (270 Bloom Mesh 10), Refined Sugar, Glucose
Corn Syrup, Citric Acid, Lactic Acid, Water, Natural Mango Flavor
M38630, Tartaric Acid, Refined Sugar

TABLE 10

Candy formulation

Active Ingredients
AC3 complex (Curcumin BD3 Complex)
Excipients
BioPerine ®, Sucrose, Liquid Glucose, Flavoring agent, Menthol,
Acidulants (Citric acid/Tartaric Acid/Maleic Acid), Purified water

TABLE 11

Tablet

Active Ingredients
Bisdemethoxycurcumin (BDMC)
Excipients
Microcrystalline cellulose, Colloidal silicon dioxide, Magnesium stearate, BioPerine ®, Polyvinylpyrrolidone/starch/Hydroxy propyl methyl cellulose, Hydroxy propyl cellulose

TABLE 12

Capsule

Active Ingredients
Bisdemethoxycurcumin (BDMC)
Excipients
Microcrystalline cellulose, BioPerine ®

TABLE 13

Powder

Active Ingredients
Bisdemethoxycurcumin (BDMC)
Excipients
BioPerine ®,

TABLE 14

Gummy formulation

Active Ingredients
Bisdemethoxycurcumin (BDMC)
Excipients
BioPerine ®, Gelatin (270 Bloom Mesh 10), Refined Sugar, Glucose Corn Syrup, Citric Acid, Lactic Acid, Water, Natural Mango Flavor M38630, Tartaric Acid, Refined Sugar

TABLE 15

Candy formulation

Active Ingredients
Bisdemethoxycurcumin (BDMC)
Excipients
BioPerine ®, Sucrose, Liquid Glucose, Flavoring agent, Menthol, Acidulants (Citric acid/Tartaric Acid/Maleic Acid), Purified water The above formulations are merely illustrative examples, any formulation containing the above active ingredient intended for the said purpose will be considered equivalent.

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

We claim:

1. A method for the management of polycystic ovary syndrome and its associated conditions in a subject, said method comprising steps of a) identifying a mammalian female subject with polycystic ovary syndrome and b) administering an effective dose of a composition comprising 20-80% w/w bisdemethoxycurcumin, 10-35% w/w demethoxycurcumin and 10-50% w/w curcumin to the said subject to alleviate polycystic ovary syndrome.

2. The method as in claim 1, wherein the composition comprises of 30-50% w/w bisdemethoxycurcumin, 10-25% w/w demethoxycurcumin and 30-50% w/w curcumin.

3. The method as in claim 1, wherein the total curcuminoids in the composition are in the range of 20-95% w/w.

4. The method as in claim 1, wherein the associated conditions are selected from the group consisting of hormonal imbalance, obesity, hypothyroidism, hyperandrogenism, oxidative stress, inflammation, gut dysbiosis, hypercholesterolemia, cardiovascular complications, hyperglycemia and insulin resistance.

5. The method as in claim 4, wherein hormonal imbalance associated with polycystic ovary syndrome is alleviated by decreasing serum levels of Luteinizing hormone and increasing the levels of 17-β estradiol, Progesterone and Follicle Stimulating Hormone.

6. The method as in claim 4, wherein obesity associated with polycystic ovary syndrome is managed by decreasing body weight, ovarian weight and increasing the expression of serum adiponectin.

7. The method as in claim 4, wherein hypothyroidism associated with polycystic ovary syndrome is managed by decreasing the levels of thyroid stimulating hormone and increasing the serum levels of T3 and T4.

8. The method as in claim 4, wherein hyperandrogenism associated with polycystic ovary syndrome is managed by decreasing the expression of serum testosterone.

9. The method as in claim 4, wherein hyperglycemia and insulin resistance associated with polycystic ovary syndrome is managed by increasing the levels of serum Omentin-1.

10. The method as in claim 4, wherein gut dysbiosis associated with polycystic ovary syndrome is managed by increasing Ghrelin levels in the serum.

11. The method as in claim 4, wherein hypercholesterolemia, cardiovascular complications associated with polycystic ovary syndrome is managed by increasing Paraoxonase-1 levels in the serum.

12. The method as in claim 4, wherein oxidative stress associated with polycystic ovary syndrome is reduced by decreasing serum malondialdehyde levels.

13. The method as in claim 4, wherein inflammation associated with polycystic ovary syndrome is reduced by decreasing the levels of advance glycation end products (AGE).

14. The method as in claim 1, wherein the composition is formulated with stabilizing agents, bioavailability enhancers, antioxidants, pharmaceutically or nutraceutically or cosmeceutically accepted excipients, enhancers and administered orally in the form of tablets, capsules, syrups, gummies, powders, suspensions, emulsions, chewables, candies or eatables.

* * * * *